(12) United States Patent
Duconge et al.

(10) Patent No.: US 9,365,854 B2
(45) Date of Patent: Jun. 14, 2016

(54) LAR PROTEIN-SPECIFIC LIGAND

(75) Inventors: Frederic Duconge, Sceaux (FR); Agnes Cibiel, Bures su Yvette (FR)

(73) Assignee: Commissariat a l'Energie Atomique et aux Energies alternatives, Paris (FR)

( * ) Notice: Subject to any disclaimer, the term of this patent is extended or adjusted under 35 U.S.C. 154(b) by 0 days.

(21) Appl. No.: 13/993,870

(22) PCT Filed: Dec. 15, 2011

(86) PCT No.: PCT/IB2011/055710
§ 371 (c)(1),
(2), (4) Date: Jun. 13, 2013

(87) PCT Pub. No.: WO2012/080976
PCT Pub. Date: Jun. 21, 2012

(65) Prior Publication Data
US 2013/0266516 A1    Oct. 10, 2013

(30) Foreign Application Priority Data

Dec. 16, 2010   (FR) ...................................... 10 60619

(51) Int. Cl.
*A61K 49/00*   (2006.01)
*C12N 15/10*   (2006.01)
*C12N 15/115*  (2010.01)

(52) U.S. Cl.
CPC .......... *C12N 15/115* (2013.01); *A61K 49/0054* (2013.01); *C12N 15/1048* (2013.01); *C12N 2310/16* (2013.01); *C12N 2310/322* (2013.01); *C12N 2310/344* (2013.01); *C12N 2310/351* (2013.01); *C12N 2310/3517* (2013.01)

(58) Field of Classification Search
CPC ................. C12N 2310/322; C12N 2310/3533; C12N 15/1048; C12N 15/115; C12N 2310/16; C12N 2310/344; C12N 2310/351; C12N 2310/3517; A61K 49/0054
USPC .................... 424/9.1; 435/6.1, 6.12; 536/23.1
See application file for complete search history.

(56) References Cited

U.S. PATENT DOCUMENTS

2007/0134234 A1*  6/2007  Smith et al. ................. 424/133.1

FOREIGN PATENT DOCUMENTS

| WO | 2005/093097 | 10/2005 |
| WO | 2007/041317 | 4/2007 |
| WO | 2009/021684 | 2/2009 |

OTHER PUBLICATIONS

Fang et al. Acc. Chem. Res., 2010, 43 (1), pp. 48-57.*
Pestourie, Aptamers Against Extracellular Targets for in Vivo Applications, Biochimie, 87, pp. 921-930, 2005.
Tavitian, In Vivo Imaging of Oligonucleotidic Aptamers, Methods in Molecular Biology, 535, pp. 241-259, 2009.
Freiss, Protein Tyrosine Phosphatases and Breast Cancer, Critical Reviews in Oncology, 52, pp. 9-17, 2004.
Den Hertog, Receptor Protein-Tyrosine Phosphatase Signalling in Development, International Journal of Developmental Biology, 43, pp. 723-733, 1999.

* cited by examiner

*Primary Examiner* — Janet Epps-Smith
(74) *Attorney, Agent, or Firm* — Morgan, Lewis & Bockius LLP

(57) ABSTRACT

The present invention relates to an aptamer comprising a nucleic acid comprising, or consisting of: —the sequence ACUGU CCCAG UAUGA CGCGA CUGCU UAGGU GGGAU GUUUC CCAUG CCUCG (SEQ ID NO: 1), or —a sequence comprising, or consisting of, at least 25 consecutive nucleotides in a sequence having at least 80% identity with SEQ ID NO: 1, with the proviso that a nucleic acid consisting of this sequence binds to the LAR protein.

20 Claims, 6 Drawing Sheets

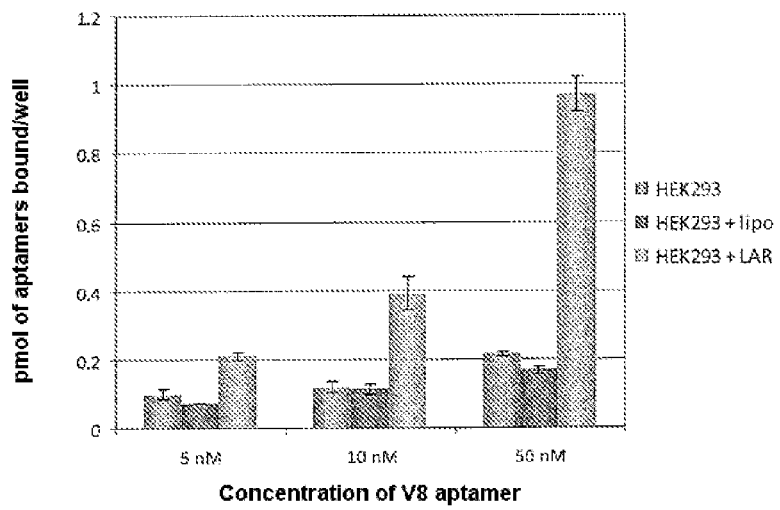
Figure 7
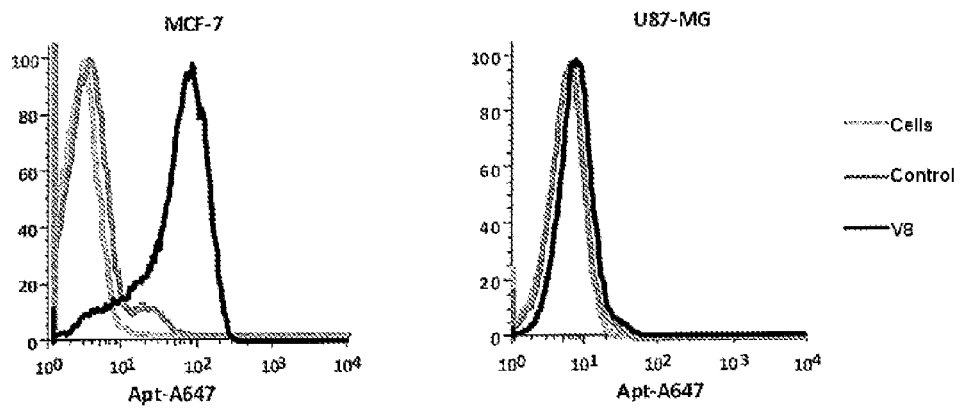
Figure 8A
Figure 8B

US 9,365,854 B2

LAR PROTEIN-SPECIFIC LIGAND

SEQUENCE LISTING SUBMISSION VIA EFS-WEB

A computer readable text file, entitled "045636-5234_SequenceListing.txt," created on or about 13 Jun. 2013, with a file size of about 18 kb contains the sequence listing for this application and is hereby incorporated by reference in its entirety.

FIELD OF THE INVENTION

The present invention relates to an LAR protein-specific ligand, and also to the diagnostic and therapeutic use thereof, or the use thereof for the in vitro detection of the LAR protein in a biological sample.

TECHNICAL BACKGROUND

Leukocyte common Antigen-Related Protein Tyrosine Phosphatase, PTP-LAR, or LAR protein, also known as protein tyrosine phosphatase, receptor type, F, PTPRF, plays an important role in mammary gland development (Schaapveld et al. (1997) Dev. Biol. 188: 134-146) and in breast cancer tumorigenesis (Freiss et al. (2004) Critical Reviews in Oncology/Hematology. 52: 9-17). It has been demonstrated, inter alia, that the expression of the LAR protein is increased in breast cancer cells, in particular breast cancer cells transformed with the ErbB-2 oncogene (Yang et al. (1999) Mol. Carcinog. 25: 139-149; LeVea et al. (2000) Breast Cancer Research and Treatment 64: 221-228). Furthermore, it would appear that the LAR protein is important for regulating the activity of several tyrosine kinase receptors (Kulas et al. (1996) J Biol Chem 271: 748-754). The LAR protein can also serve as a biomarker for predicting the response to anti-EGFR treatments for breast cancer (WO 2009/021684).

In addition, this protein is a known inhibitor of insulin activation pathways and an increased level of expression of this protein has been found in the insulin-sensitive tissues of obese individuals and insulin-resistant individuals (Ahmad et al. (1995) J Clin Invest 95: 2806-2812). Thus, it has been demonstrated that the LAR protein can contribute to pathological conditions associated with insulin resistance, such as coronary artery disease in patients suffering from type 2 diabetes (Menzaghi et al. (2008) J Intern Med 263: 653-654).

The LAR protein ligands identified to date, essentially of immunoglobulin type, have limitations, in particular in terms of synthesis cost, immunogenicity or affinity for their target.

SUMMARY OF THE INVENTION

The present invention follows from the unexpected demonstration, by the inventors, of an aptamer, of nucleotide nature, which specifically recognizes the LAR protein at the surface of cells, with a nanomolar dissociation constant.

Thus, the present invention relates to an aptamer comprising a nucleic acid capable of specifically recognizing the LAR protein at the surface of a cell.

More particularly, the invention relates to an aptamer comprising, or consisting of, a nucleic acid comprising, or consisting of:

the sequence ACUGUCCCAGUAUGACGCGACUGCUUAGGUGGGAUGUUUCCCAUGCCUCG (SEQ ID NO: 1), or a sequence comprising, or consisting of, at least 15 consecutive nucleotides of a polynucleotide having at least 60% identity with SEQ ID NO: 1, with the proviso that a nucleic acid consisting of this sequence binds to the LAR protein.

In one particular embodiment, the invention relates to the aptamer according to the invention, for use thereof as a medicament or a diagnostic agent.

The present invention also relates to a pharmaceutical or diagnostic composition comprising, as active substance, at least one aptamer according to the invention, in association with at least one pharmaceutically acceptable vehicle.

In this respect, the invention also relates to an in vitro method for diagnosis of a cancer in an individual, comprising the following steps:
  bringing the biological sample into contact with an aptamer according to the invention;
  determining the amount of aptamer bound in the sample;
  optionally, comparing the amount of aptamer bound in the sample with at least one predetermined value;
  deducing therefrom whether the individual is suffering from a cancer.

The present invention also relates to a method for diagnosis of a cancer in an individual, comprising the following steps:
  administering an aptamer according to the invention to the individual;
  detecting, quantifying and/or localizing the aptamer in the individual or a part of the individual;
  deducing therefrom whether the individual is suffering from a cancer.

The present invention also relates to the in vitro use of an aptamer according to the invention, for detecting the presence of LAR protein, or determining the amount of LAR protein, present in a biological sample.

The present invention also relates to an in vitro method for detecting or determining the amount of LAR protein in a biological sample, comprising the following steps:
  bringing the biological sample into contact with an aptamer according to the invention;
  quantifying or detecting the presence or absence of aptamer bound in the sample;
  deducing therefrom the amount or the presence or absence of LAR protein in the sample.

The present invention also relates to a method for detecting, quantifying or localizing LAR protein, in an individual or a part of an individual, comprising the following steps:
  administering an aptamer or a diagnostic composition as defined above to the individual;
  detecting, quantifying and/or localizing the aptamer in the individual or a part of the individual;
  deducing therefrom the presence or absence, the amount and/or the localization of LAR protein in the individual or the part of the individual.

The present invention also relates to the use of an aptamer as defined above, for screening for LAR protein ligands.

The present invention also relates to a method for screening for LAR protein ligands comprising the following steps:
  bringing together LAR protein and, concomitantly or successively, a ligand to be screened and an aptamer as defined above;
  determining the amount of aptamer bound to the LAR protein;
  deducing therefrom whether the ligand is an LAR protein ligand.

DETAILED DESCRIPTION OF THE INVENTION

As is intended herein, an "aptamer" denotes a compound, comprising at least one nucleic acid, capable of binding specifically to a target, in particular of a protein nature, by means of the nucleic acid. An aptamer is said to bind specifically to a target when it exhibits essentially no affinity for a compound which is structurally unrelated to the target. Preferably, in the case of a protein target, a protein compound is said to be structurally unrelated to the target according to the invention when the sequence identity between the target and the compound is less than 60%, preferably less than 70% and more preferably less than 80%. Preferably, according to the invention, an aptamer is said to exhibit essentially no affinity for a compound according to the invention, in particular when the dissociation constant of the aptamer with respect to the compound is greater than $10^{-6}$ mol/l and preferably greater than $10^{-7}$ mol/l. The dissociation constant can in particular be determined, under standard conditions, using the Scatchard and Lineweaver Burk representations well known to those skilled in the art.

Advantageously, the aptamer according to the invention is specific for the LAR protein, in particular for the human LAR protein, especially when the LAR protein is expressed at the surface of a cell. The LAR protein, or leucocyte common antigen-related protein tyrosine phosphatase, PTP-LAR, also known as protein tyrosine phosphatase, receptor type, F, PTPRF, is well known to those skilled in the art. The human LAR protein is in particular described under reference P10586 in the GenBank database. By way of example, the human LAR protein is represented by the sequence SEQ ID NO: 3.

The aptamer according to the invention can also comprise at least one additional group in addition to the nucleic acid. Thus, the nucleic acid according to the invention can be bonded to at least one additional group. However, preferentially, the aptamer according to the invention consists of the nucleic acid according to the invention and of at least one additional group according to the invention.

The additional group according to the invention can be of any type and of any nature. The additional group according to the invention can thus be a radioisotope, an organic molecule comprising at most 100 carbon atoms, a nanoparticle, in particular a micelle, a protein, in particular a glycoprotein, a carbohydrate, a lipid, or else a polynucleotide. According to the invention, it is, however, preferred for the additional group according to the invention to be selected from the group consisting of a detectable label, a pharmacological compound, and a compound capable of modifying the pharmacokinetic characteristics of a nucleic acid to which it is bonded, such as polyethylene glycol (PEG).

The detectable label according to the invention can be of any type; it can in particular be a fluorophore, for example fluorescein or luciferase; a radioisotope, in particular suitable for scintigraphy, for example $^{99m}$Tc; an antibody-recognizable tag, for example the c-Myc protein; an affinity tag, for example biotin; or an enzyme, for example horseradish peroxidase.

The pharmacological compound according to the invention can also be of any type; it is in particular an anticancer chemotherapy agent, such as a cytostatic or cytolytic agent. The pharmacological compound according to the invention can also be of any nature; it can in particular be a platinum derivative, an organic molecule comprising less than 100 carbon atoms, a peptide, a nucleotide analog, a toxin, an interfering RNA or an antisense oligonucleotide.

Preferably, the nucleic acid according to the invention is RNA. As will become clearly apparent to those skilled in the art, it is quite particularly preferable for the nucleic acid according to the invention to be single-stranded. It is also quite particularly preferable for the nucleic acid according to the invention to have a three-dimensional structure which allows it to bind specifically to the LAR protein. Moreover, the backbone or the ribose of the nucleic acid according to the invention can be totally or partially modified, especially so as to make it resistant to hydrolytic degradation, in particular due to the action of nuclease, especially when the nucleic acid is RNA. Such modifications are well known to those skilled in the art and cover, in particular, modifications of the OH function on the carbon in the 2' position of the ribose by methylation, or the substitution of this OH function with an amino group or with a halogen, in particular with fluorine, and also recourse to a phosphorothioate backbone, or to structures of locked nucleic acid (LNA) or peptide nucleic acid (PNA) type. Thus, preferably, the nucleic acid according to the invention is an RNA in which the riboses of the pyrimidine nucleotides bear a fluorine atom on the carbon in the 2' position, it being possible for the riboses of the purine nucleotides to be unchanged.

A sequence having at least 60% nucleotide identity with SEQ ID NO: 1 according to the invention differs in particular from SEQ ID NO: 1 by virtue of the insertion, the deletion or the substitution of at least one nucleotide. As it is intended herein, the percentage identity between two sequences is defined as the number of positions for which the bases are identical when the sequences are optimally aligned, divided by the total number of bases of the larger of the two sequences. Two sequences are said to be optimally aligned when the percentage identity is at a maximum. Moreover, as will become clearly apparent to those skilled in the art, it may be necessary to call upon additions of gaps so as to obtain an optimal alignment between the two sequences.

A nucleic acid is said to bind to the LAR protein if the dissociation constant of the nucleic acid with respect to the LAR protein, in particular the human LAR protein, preferably expressed by a cell, in particular a cell of the MCF-7, A-431, MDA-MB-231, HEK293, HEK293-KDR, 4T1 or EMT6 cell line, as is illustrated in the examples, is less than $10^{-6}$ mol/l, preferably less than $10^{-7}$ mol/l and more preferably less than $10^{-8}$ mol/l.

As will be clearly apparent to those skilled in the art, when the aptamer according to the invention comprises a nucleic acid according to the invention, it can also comprise other nucleic acids. On the other hand, when the aptamer according to the invention consists of the nucleic acid according to the invention it does not comprise other nucleic acids. Similarly, when the nucleic acid according to the invention comprises a sequence, it can also comprise additional sequences extending from the 5' and/or 3' side of the sequence in question. On the other hand, when the nucleic acid according to the invention consists of a sequence, it does not comprise additional sequences in addition to the sequence in question.

A sequence comprising SEQ ID NO: 1 according to the invention can in particular comprise sequences on the 5' and/or 3' side aimed at structuring the nucleic acid. It is thus preferred for the nucleic acid according to the invention to comprise, or to consist of, SEQ ID NO: 2. In this context, the invention then also relates, in particular, to a nucleic acid comprising, or consisting of, at least 15 consecutive nucleotides of a sequence having at least 60% identity with SEQ ID NO: 2, with the proviso that a nucleic acid consisting of this sequences binds to the LAR protein.

Preferably, the sequence comprising, or consisting of, at least 15 consecutive nucleotides of a sequence having at least 60% identity with SEQ ID NO: 1 or 2 according to the invention comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 60% identity with SEQ ID NO: 1 or 2.

Likewise preferably, the sequence comprising, or consisting of, at least 15 consecutive nucleotides of a sequence having at least 60% identity with SEQ ID NO: 1 or 2 according to the invention comprises or consists of at least 15 consecutive nucleotides of a sequence having at least 65%, 70%, 75%, 80%, 85%, 90%, 95% or 100% identity with SEQ ID NO: 1 or 2 according to the invention.

More preferably, the sequence comprising, or consisting of, at least 15 consecutive nucleotides of a sequence having at least 60% identity with SEQ ID NO: 1 or 2 according to the invention comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 80% identity with SEQ ID NO: 1 or 2.

Preferably still, the sequence comprising, or consisting of, at least 15 consecutive nucleotides of a sequence having at least 60% identity with SEQ ID NO: 1 or 2 according to the invention comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 85% identity with SEQ ID NO: 1 or 2.

Even more preferably, the sequence comprising, or consisting of, at least 15 consecutive nucleotides of a sequence having at least 60% identity with SEQ ID NO: 1 or 2 according to the invention comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 90% identity with SEQ ID NO: 1 or 2.

Particularly preferably, the sequence comprising, or consisting of, at least 15 consecutive nucleotides of a sequence having at least 60% identity with SEQ ID NO: 1 or 2 according to the invention comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 95% identity with SEQ ID NO: 1 or 2.

Moreover, alternatively, the sequence comprising, or consisting of, at least 15 consecutive nucleotides of a sequence having at least 60% identity with SEQ ID NO: 1 or 2 according to the invention can consist of a sequence of 95 nucleotides having at least 60%, 65%, 70%, 75%, 80%, 85%, 90% or 95% identity with SEQ ID NO: 2, and a nucleic acid consisting of this sequence is capable of adopting the structure of formula (I) below:

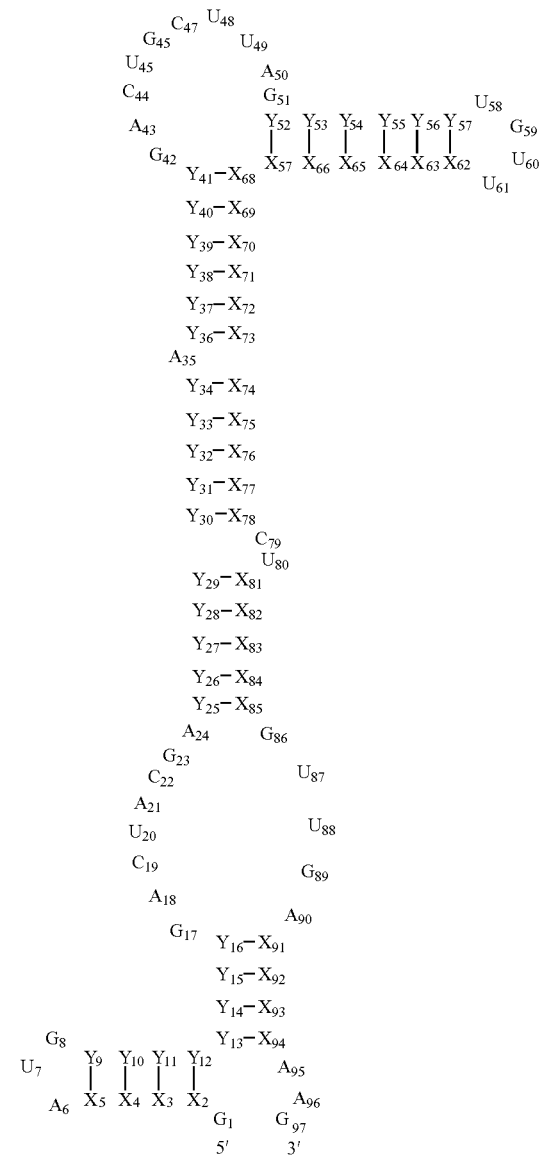

in which:
A, C, G and U are the ribonucleotides adenosine, cytidine, guanosine and uridine;
each one of the X and of the Y, which may be identical or different, represents A, C, G or U;
each of the pairs X-Y or Y-X, which may be identical or different, represent A-U, U-A, G-C, C-G, G-U or U-G pairs.

Those skilled in the art can easily determine the secondary structure capable of being adopted by a nucleic acid having a sequence according to the invention, for example by means of modeling algorithms or software well known to those skilled in the art, such as mfold (version 3.4) described in *Nucleic Acids Res.* (2003) 31: 3406-15 and vsfold5 RNA Pseudoknot Prediction described in *PLoS One* (2007), 2:905. In this respect, the inventors have established, by means of such modeling tools, that the V8 aptamer of sequence SEQ ID NO: 2, which is described in the examples, adopts a structure of formula (I).

When the aptamer according to the invention is used as a medicament or is included in a pharmaceutical composition, it is in particular useful for inhibiting angiogenesis, and also for the prevention or treatment, in particular by inhibiting angiogenesis, of cancers, and of diseases involving ocular neovascularization, such as age-related macular degeneration and diabetic retinopathy. Moreover, when it is used as a medicament or is included in a pharmaceutical composition, the aptamer according to the invention is also useful for the treatment of metabolic diseases, in particular insulin resistance, diabetes, especially type 2 diabetes, metabolic syndrome or cardiovascular diseases, such as coronary artery disease, in particular in patients suffering from type 2 diabetes.

When the aptamer according to the invention is used as a diagnostic agent or is included in a diagnostic composition, it is in particular useful for the diagnosis of cancers or of metabolic diseases, such as insulin resistance.

Preferably, in the methods for detection or diagnosis according to the invention, the detection of aptamer bound in the sample is carried out by performing a polymerase chain reaction (PCR) intended to amplify the aptamer, in particular an RT-PCR (PCR comprising a reverse transcription step). Preferably, when the nucleic acid according to the invention comprises SEQ ID NO: 2, the PCR is performed using the pair of primers of sequences CTTGTCATCAACCTGC-CAGCCAGT (SEQ ID NO: 4) and GGGAGATGCTCTGT-CAGACTACG (SEQ ID NO: 5) or the pair of primers having the sequences complementary to SEQ ID NO: 4 and SEQ ID NO: 5. Moreover, the invention also relates to a nucleic acid comprising or consisting of SEQ ID NO: 4 or SEQ ID NO: 5 or the sequences complementary to SEQ ID NO: 4 or SEQ ID NO: 5.

Likewise preferably, in the methods for detection or diagnosis according to the invention, when the aptamer is administered to an individual, it is preferred for the aptamer to be detectable by means of in vivo imaging methods, which are in particular external, such as planar or three-dimensional (3D) fluorescent imaging, or internal, such as endoscopy, for example.

Moreover, the present invention also relates to an LAR protein ligand for use thereof as an angiogenesis inhibitor, and also for the prevention or treatment, in particular by inhibiting angiogenesis, of cancers, and of diseases involving ocular neovascularization, such as age-related macular degeneration and diabetic retinopathy. The LAR protein ligand according to the invention can be of any type; it can in particular be an antibody or an antibody fragment comprising the antigen-binding part or paratope, a single-chain Fv (scFv) fragment, or else an aptamer, in particular, as has been indicated above, an aptamer according to the invention.

DESCRIPTION OF THE FIGURES

FIG. 1 represents the protocol for the selection of the aptamers used by the inventors in order to obtain the V8 aptamer.
FIG. 2 represents the secondary structure of the V8 aptamer predicted using the mfold program (version 3.4, http://mfold.bioinfo.rpi.edu/cgi-bin/rna-form1.cgi). On this structure, the fixed sequences which enable a PCR amplification have been highlighted in gray.
FIG. 3 represents the protocol for identifying the target of the V8 aptamer. Briefly, the biotinylated aptamer is incubated on MCF-7 cells in suspension. After several washes, streptavidin-coupled magnetic beads are added. Only the cells which have bound the biotinylated V8 aptamer will be retained on the beads. The cells are then lysed and the proteins retained by the V8 aptamer are eluted. The proteins are then loaded on an SDS-PAGE gel and the specific bands are analyzed by mass spectrometry.

FIG. 4 is a photograph of an SDS-PAGE gel on which the eluates originating from beads brought directly into contact with the cells (beads), a control oligonucleotide (control sequence) or the V8 aptamer are migrated. The main band corresponding to the eluate originating from the aptamer is indicated. The band corresponding to bovine serum albumin (BSA), used as a nonspecific competitor, is also represented. Briefly, the proteins are loaded onto an SDS 10%-PAGE gel. The gel is then stained using the proteosilver silver stain kit (Sigma). The interesting bands are cut out, destained with the same kit and analyzed by mass spectrometry.

FIG. 5 is an autoradiograph of an SDS 10%-PAGE gel on which are migrated cell lysates of HEK293-KDR cells placed in the presence of the V1, V8 and V10 aptamers or the naïve library (NL) radiolabeled and bridged by UV irradiation. The aptamer alone, for its part, migrates at around 37 kDa (Apta lane). The arrow indicates the main protein bridged by the V8 aptamer, the size of which corresponds to that of the LAR protein. Briefly, the aptamers and the naïve library were incubated on the cells at a concentration of 25 nM. After 15 minutes of incubation at 37° C., the sequences not associated with the cells were eliminated. The UV-bridging was carried out with an irradiation energy of 800 000 µJ/cm², and the cells were then lysed and the proteins were loaded on a 10% gel.

FIG. 6 represents the amount of V8 aptamers bound per well (y-axis, pmol) containing untransfected HEK293 cells (0), untransfected HEK293 cells placed in the presence of lipofectamine (0(+lipo)), or HEK293 cells transfected with 0.25 µg, 0.5 µg, 0.75 µg or 1 µg of plasmid expressing the LAR protein (x-axis). The radiolabeled aptamer is incubated at a concentration of 10 nM for 15 minutes. After several washes, the radioactivity bound to the cells is counted and the amount of aptamers bound is determined (in pmol/well).

FIG. 7: effect of the overexpression of the LAR protein on the binding of the V8 aptamer
FIG. 7 represents the amount of V8 aptamers bound per well (y-axis, pmol) containing untransfected HEK293 cells (0), untransfected HEK293 cells placed in the presence of lipofectamine (0) (+lipo)), or HEK293 cells transfected with a plasmid expressing the LAR protein, in the presence of 5 nM, 10 nM and 50 nM of V8 aptamer (x-axis). The radiolabeled aptamers are incubated for 15 minutes. After several washes, the radioactivity bound to the cells is counted and the amount of aptamers bound is determined (in pmol/well).

FIGS. 8A and 8B: study of the binding of the V8 aptamer to MCF-7 and U87-MG cells by flow cytometry
FIGS. 8A and 8B represent the amount of MCF-7 cells (FIG. 8A) and U87-MG cells (FIG. 8B) sorted by flow cytometry (y-axis, as percentage of maximum fluorescence) as a function of the fluorescence emitted by the V8 aptamer (black curve), the control sequence (dark gray curve) and the cells alone (light gray curve) (x-axis, arbitrary units). The cells were incubated with the aptamers at a concentration of 5 nM for 30 minutes, washed and analyzed by FACS. 100 000 events were counted for each condition.

FIG. 9 represents images, acquired on a Tomofluo 3D instrument, of "nude" mice having developed tumors after a xenograft of MCF-7 cells, which were injected intravenously with 1.4 nmol of V8 aptamer (upper part of the figure, V8) or of control sequence (lower part of the figure, Ctrl) labeled with Alexa Fluor 680. The images were acquired between 5 and 180 minutes after injection. The tumor and the reference zone which makes it possible to measure the ratio of signal in the tumor/internal reference are indicated.

FIG. 10 represents the amount of fluorescence determined in triplicate as a percentage of the dose injected (% DI, y-axis) in the tumor for the V8 aptamer and a control sequence.

FIG. 11 represents the number of tubes per node of cells on four randomly chosen fields of view (y-axis), in the absence of oligonucleotide (control), in the presence of a control sequence, and in the presence of the V8 aptamer (x-axis).

EXAMPLES

Example 1

Obtaining the V8 Aptamer Specific for the LAR Protein

Figure 1:
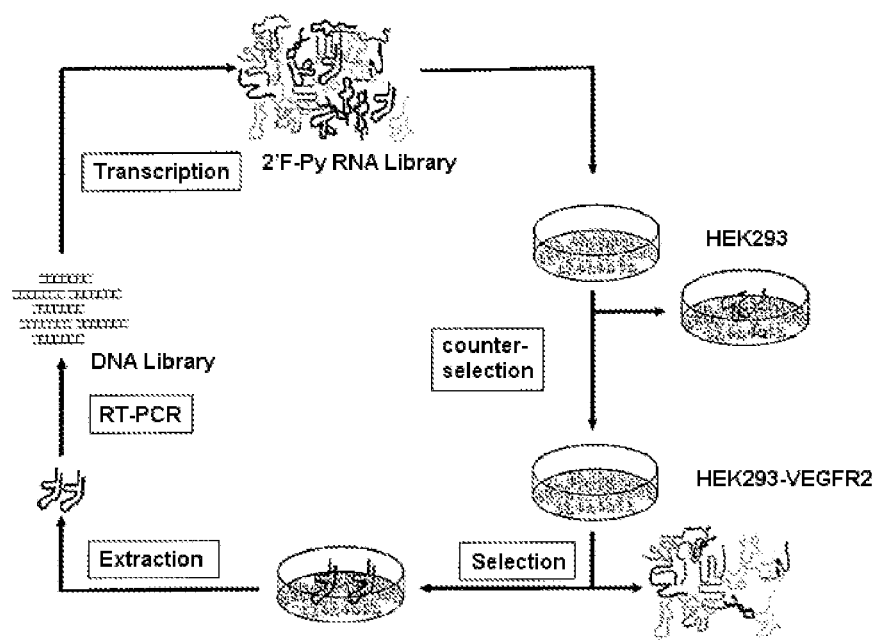
FIG. 1: selection protocol diagram

1—Identification of the V8 Aptamer after 17 Rounds of Selection on HEK293-VEGFR2 Cells The inventors used the SELEX technique, in particular described in application WO 2005/093097, for the purpose of selecting aptamers against the VEGFR2 receptor (vascular endothelial growth factor receptor 2). For this, HEK293 cells overexpressing VEGFR2 and, for the counterselection, HEK293 cells not expressing VEGFR2, were used (FIG. 1).

During this SELEX, the inventors varied various parameters for the purpose of gradually increasing the selection pressure (table 1). Compared with the protocol described in application WO 2005/093097, the inventors introduced a few modifications: during a few rounds, the inventors changed cell type for the purpose of increasing the specificity. For these rounds, the inventors used porcine aortic endothelial (PAE) cells stably transfected so as to express VEGFR2 (PAE-VEGFR2) for the selection, and non-transfected porcine endothelial cells (PAE) for the counterselection (rounds 13 and 14). Furthermore, the inventors inverted the selection and counterselection step (rounds 16 and 17). Finally, throughout the selection process, VEGFR, which is the VEGFR2 receptor ligand, was added 10 minutes before the end of the incubation with the library, at each round of SELEX. This was for the purpose of selecting aptamers which are not detached by VEGF. The selection conditions are given in table 1 below:

TABLE 1 evolution of the selection pressure during the SELEX

| Cycle | Cell type | CS: Number of cells (million) | S: Number of cells (million) | Inversion CS and S | Incubation volume (ml) | [ ] of 2'F-Py RNA (μM) | Incubation time (min) | Number of washes | Specific washing condition | tRNa |
|---|---|---|---|---|---|---|---|---|---|---|
| 1 | HEK293 | 10 | 10 | | 3 | 1 | 30 | 3 | | |
| 2 | HEK293 | 10 | 10 | | 3 | 1 | 30 | 3 | | |
| 3 | HEK293 | 10 + 10 | 10 | | 3 | 1 | 25 | 3 | | |
| 4 | HEK293 | 5 + 5 | 5 | | 3 | 1 | 25 | 4 | | |
| 5 | HEK293 | 5 + 5 | 5 | | 3 | 1 | 20 | 4 | | |
| 6 | HEK293 | 5 + 5 | 5 | | 3 | 1 | 20 | 5 | | |
| 7 | HEK293 | 5 + 5 | 5 | | 3 | 1 | 20 | 5 | | |
| 8 | HEK293 | 5 + 5 | 5 | | 3 | 1.5 | 20 | 5 | W5: 5 min | |
| 9 | HEK293 | 5 + 5 | 5 | | 3 | 1.5 | 20 | 5 | W5: 5 min | |
| 10 | HEK293 | 5 + 5 | 5 | | 3 | 1 | 20 | 5 | W5: 5 min | |
| 11 | HEK293 | 5 + 5 | 5 | | 3 | 1.5 | 20 | 5 | W5: 5 min | + |
| 12 | HEK293 | 5 + 5 | 5 | | 3 | 1 | 20 | 5 | W5: 5 min | + |
| 13 | PAE | 5 + 5 | 5 | | 3 | 2 | 20 | 5 | W5: 5 min | + |
| 14 | PAE | 5 + 5 | 5 | | 3 | 0.5 | 20 | 5 | W5: 5 min | + |
| 15 | HEK293 | 5 + 5 | 5 | | 3 | 2 | 20 | 5 | W5: 5 min | + |
| 16 | HEK293 | 5 | 5 | + | 3 | 2 | 20 | 5 | W5: 5 min | + |
| 17 | HEK293 | 5 | 5 | + | 3 | 1.5 | 20 | 5 | W5: 5 min | + |

S: Selection,
CS: Counterselection,
W: Wash

The library resulting from round 17 was cloned and sequenced. The inventors tested the affinity of about thirty sequences for the HEK293-VEGFR2 cells at 25 nM. This allowed them to identify three particularly interesting aptamers with a strong affinity for these cells, V1, V8 and V10. However, these aptamers also bind to HEK293 cells, which do not express the target, indicating that the target of these aptamers is not VEGFR2. The inventors then chose to continue the characterization of the V8 aptamer, which has the strongest affinity for the cells (Kd ~5.3 nM).

2. Sequence of the V8 Aptamer:

The sequence of the V8 aptamer is the following:

```
                                          (SEQ ID NO: 2)
5' GGGAGAUGCUCUGUCAGACUACGACUGUCCCAGUAUGACGCGACU
GCUUAGGUGGGAUGUUUCCCAUGCCUCGACUGGCUGGCAGGUUGAUGA
CAAG 3'.
```

It should be noted that, in order to improve the nuclease resistance of the V8 aptamer, the riboses of the pyrimidines bear a fluorine atom on the carbon in the 2' position (the riboses of the purines bear, for their part, as is the case in natural RNA, a hydroxyl function (OH) on the carbon in the 2' position).

Figure 2:
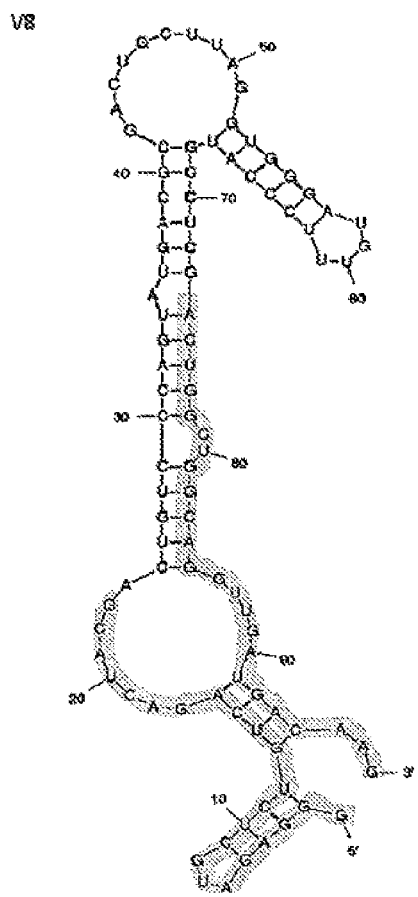
FIG. 2: V8 aptamer structure prediction

FIG. 2 represents a secondary structure prediction formed using the mfold software (version 3.4) (*Nucleic Acids Res.* (2003) 31: 3406-15).

3. Validation of the Use of the V8 Aptamer for Establishing a Profile of Expression at the Surface of Various Cell Lines The affinity and the Cmax of the V8 aptamer were determined for various cancer cell lines (table 2).

TABLE 2 affinity and number of targets per cell
of the V8 aptamer for various cell lines

| Species | Cell type | Kd (nm) | Cmax (pM) | Number of targets/cell |
|---------|-----------|---------|-----------|------------------------|
| Human   | MCF-7     | 1.6 ± 0.6 | 251 ± 40  | 138 100 ± 21 800 |
|         | A-431     | 5.6 ± 0.6 | 455 ± 21  | 134 300 ± 6100   |
|         | MDA-MB-231 | 3 ± 0.4  | 131 ± 12  | 77 800 ± 7200    |
|         | U87-MG    | —       | —         | —                      |
|         | HEK293    | 3.8 ± 0.9 | 264 ± 52  | 80 000 ± 15 600  |
|         | HEK293-KDR | 5.3 ± 1.5 | 119 ± 6  | 46 000 ± 2200    |
| Mouse   | 4T1       | 2.9 ± 0.1 | 167 ± 13  | 65 200 ± 4900    |
|         | EMT6      | 2.8 ± 0.6 | 129 ± 24  | 42 400 ± 8000    |
| Rat     | PC12-MEN-2A | 34.9 ± 4.4 | 764 ± 112 | 141 400 ± 20 800 |

The binding curves were obtained for each cell type. From the specific binding, and using the Scatchard representation, the Kd and the Cmax were calculated for each cell type. Knowing the Cmax and the number of cells during the binding, the inventors were able to deduce therefrom an approximate number of targets per cell.

The V8 aptamer has an affinity of approximately 3 nM for most of the cell lines, except for the PC12-MEN-2A cells for which it has an affinity of 35 nM and the U87-MG cells for which it has no affinity. Interestingly, the target of the V8 aptamer appears to be very abundant at the surface of the MCF-7 breast cancer line and at the surface of the A-431 epidermal cancer line overexpressing EGFR.

4. Identification of the Target of the V8 Aptamer a. Protocol for Purifying the Target of the Aptamer In order to identify the target of the V8 aptamer, a protocol derived from Berezovski et al. (2008) *J. Am. Chem. Soc., Aptamer-Facilitated Biomarker Discovery* (AptaBiD) was used, in which BSA was added as a competitor in order to prevent the nonspecific binding of proteins to the beads. The protocol is summarized in FIG. 3.

b. SDS-PAGE Gel and Mass Spectrometry

Figure 3:
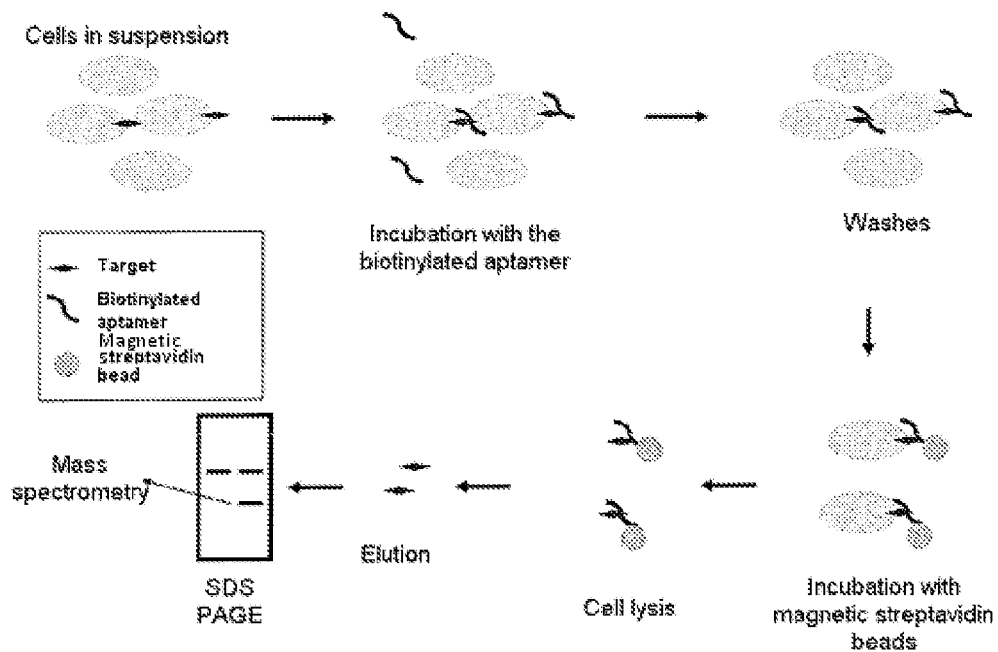
FIG. 3: protocol for identifying the target of the V8 aptamer
Figure 4:
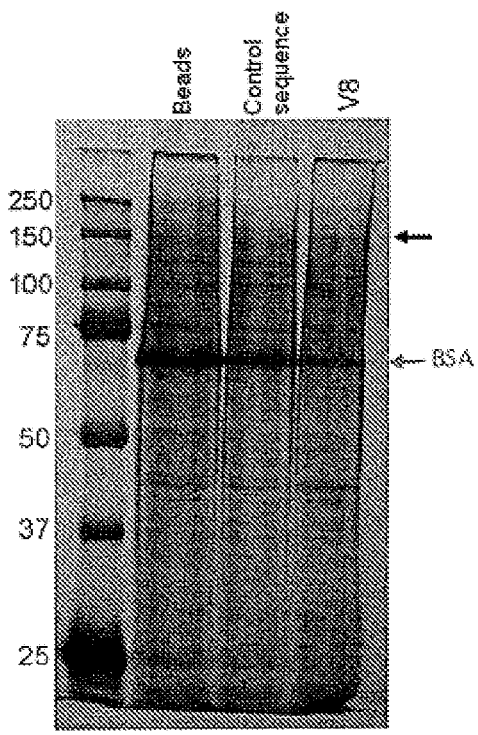
FIG. 4: protein migration by SDS-PAGE electrophoresis

The proteins eluted at the end of the protocol summarized in FIG. 3 were analyzed by electrophoresis (FIG. 4). A V8 aptamer-specific band was identified. This band was cut out and analyzed by mass spectrometry. The peptides of about twenty proteins were detected in the gel fragment. Among them, one protein was identified as being liable to correspond to the target of the V8 aptamer. This protein was identified as being protein tyrosine phosphatase, receptor type, F (PTPRF) also known as leukocyte common antigen-related (LAR) protein. It is a membrane protein of 213 kDa.

c. Validation of the Target of the V8 Aptamer

In order to verify that the V8 aptamer interacts with the LAR protein, the inventors first of all carried out UV-bridging experiments.

UV irradiation can induce the formation of covalent bonds at the level of points of contact that exist between a protein and a nucleic acid (Zhang et al. (2004) *Biochem Biophys Res Commun* 322: 705-711).

Figure 5:
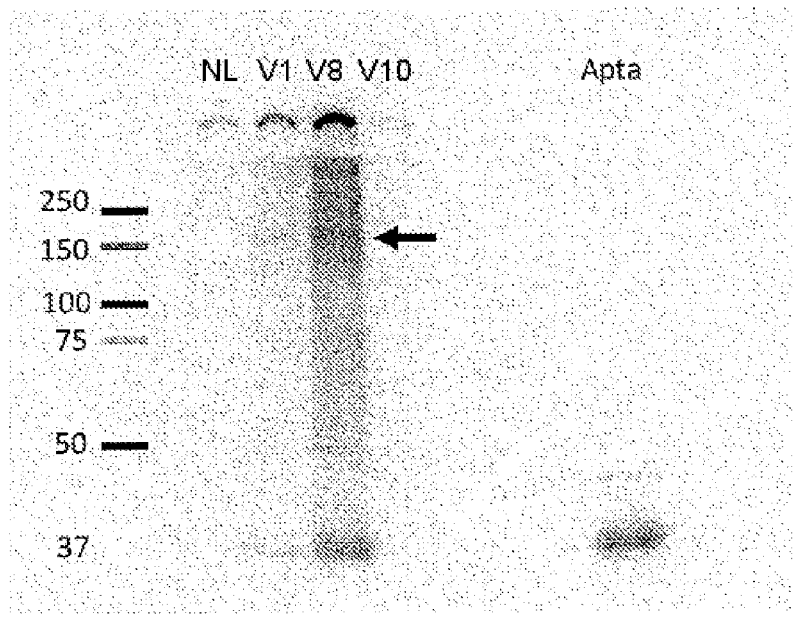
FIG. 5: UV-bridging of the V1, V8 and V10 aptamers

The V1, V8 and V10 aptamers, and also the naïve library, which were radiolabeled, were incubated for 15 minutes on the cells and then the cells were UV-irradiated. The proteins were then extracted and loaded on an SDS 10%-PAGE gel. Interestingly, the V8 aptamer was bridged to a protein of which the size corresponds to that of the LAR protein (FIG. 5).

A second validation was carried out using an expression plasmid for the longest isoform of the LAR protein. HEK293 cells were used to carry out the transfection by means of lipofectamine 2000 (Invitrogen). Several amounts of plasmid were transfected (0.25 µg-1 µg). 48 Hours later, 10 nM of radiolabeled V8 aptamer or of radiolabeled control sequence were incubated with the cells. After several washes, the radioactivity associated with the cells was counted.

Figure 6:
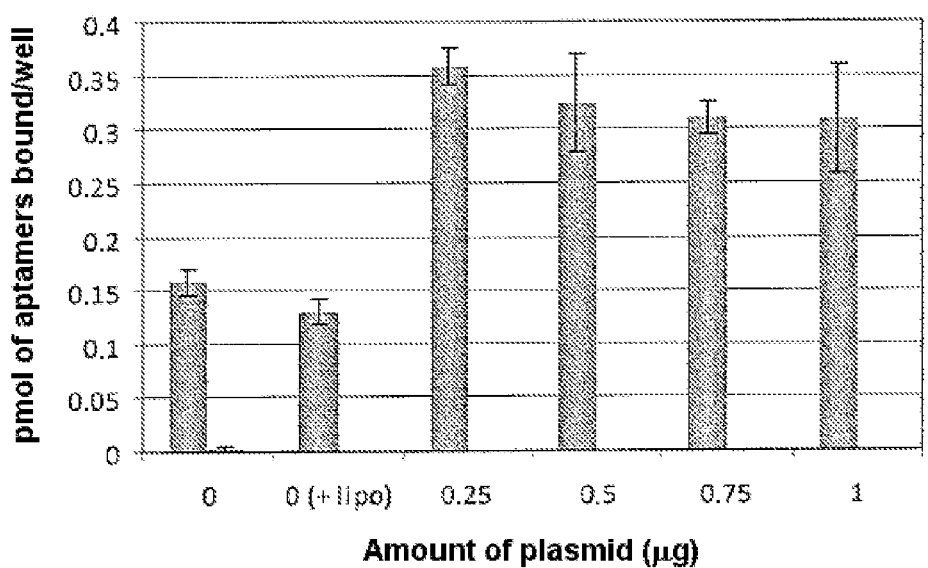
FIG. 6: effect of the overexpression of the LAR protein on the binding of the V8 aptamer

The V8 aptamer exhibits affinity for HEK293 cells (table 2 and FIG. 6). However, the binding of the V8 aptamer is at least twice as great when these cells were transfected with the expression plasmid for the LAR protein. It is observed that the binding does not increase when the amount of plasmid transfected is increased, thereby indicating that 0.25 µg of plasmid is sufficient to have a maximum expression.

When the cells were treated with lipofectamine without the addition of plasmid, the binding of the V8 aptamer is identical to that obtained with untreated cells, thereby indicating that the increase in the binding is indeed due to the expression of the plasmid and not due to the presence of the lipofectamine.

In order to confirm this result, the experiment was reproduced, by transfecting 0.25 µg of plasmid and by testing various concentrations of V8 aptamer (FIG. 7).

As previously, an increase in the binding of the V8 aptamer is observed when the cells were transfected with the plasmid expressing the LAR protein. This increase in binding is visible regardless of the concentration of aptamer used. It is noted that, the higher the concentration of aptamers incubated, the greater the binding of the aptamer compared with the untransfected cells (5 times more binding at 50 nM compared with twice as much binding at 5 nM).

All these results demonstrate that the target of the V8 aptamer must be the LAR protein.

Example 2

Use of the V8 Aptamer in FACS

The V8 aptamer and the control sequence (SEQ ID NO: 6), labeled with AlexaFluor 647 (Invitrogen), were incubated with the MCF-7 cells and the U87-MG cells (FIGS. 8A and 8B).

Whether on the MCF-7 cells or the U87-MG cells, it is observed that the control sequence does not bind to the cells since the fluorescence intensity is identical to that obtained for the cells alone. The V8 aptamer binds to the MCF-7 cells, but no increase in fluorescence is observed on the U87-MG cells. These results are in agreement with the binding experiments described above.

Example 3

Use of the V8 Aptamer in Imaging

In order to evaluate whether the V8 aptamer can enable tumor targeting in vivo, the inventors carried out fluorescence imaging experiments in mice. For this, the inventors used an imaging instrument (TomoFluo3D, LETI, Grenoble, France). This instrument allows semi-quantitative measurements by planar imaging and quantitative measurements by tomography (Garofalakis et al. (2010) *Optics Letters* 35: 3024-3026). These experiments were carried out with athymic "nude" mice. MCF-7 cells were used in order to carry out xenografts in these mice. From 2 weeks to 2 months after the subcutaneous injection of the cells at the top of the back, the xenografts obtained reach volumes of about one hundred mm$^3$. Aptamer biodistribution experiments can then be carried out by optical imaging.

The biodistribution of the V8 aptamer was compared with that of a control sequence in MCF-7 xenografts. For this, the sequences labeled with Alexa Fluor 680 (1.4 nmol) were injected into the mice in the caudal vein. The planar imaging was carried out between 1 minute and 3 hours after the injection and the three-dimensional imaging was carried out in the tumors at time 3 hours in order to be able to quantify the amount of aptamers having reached the tumor.

1. Planar Imaging

Figure 9:
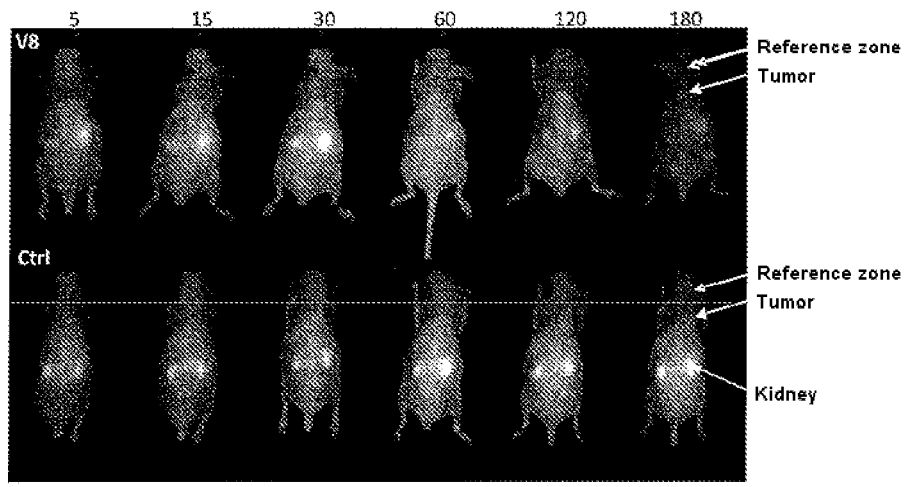
FIG. 9: biodistribution of the V8 aptamer and of a control sequence in "nude" mice having developed tumors after a xenograft of MCF-7 cells

Following the intravenous injection of the V8 aptamer or of the control sequence, images were taken at various times post-injection. For each sequence, 3 mice were injected. FIG. 9 represents, respectively, the biodistributions of the V8 aptamer and of the control sequence in a mouse.

As expected, the sequences are rapidly eliminated in the urine and by the hepatobiliary system. Moreover, using these images obtained, and for each of the mice, regions of interest (ROIs) were traced at the level of the tumor and at the level of the head between the two ears (reference zone) using the ImageJ software (MacBiophotonics). The mean fluorescence intensity was then calculated for each ROI. The background noise was subtracted (autofluorescence of the mouse, measured using a photograph taken before injection) and the ratio between the fluorescence in the tumor and the fluorescence in the head was calculated over time. The means of these ratios over time are indicated in table 3.

TABLE 3 ratio of the fluorescence intensity
in the tumor/reference zone over time

| Time (min) | Control | V8 | |
|---|---|---|---|
| 5 | 1.10 ± 0.12 | 1.29 ± 0.12 | ns |
| 10 | 1.17 ± 0.10 | 1.39 ± 0.09 | ns |
| 15 | 1.18 ± 0.04 | 1.51 ± 0.04 | * |
| 30 | 1.32 ± 0.08 | 1.66 ± 0.07 | * |
| 60 | 1.42 ± 0.09 | 1.73 ± 0.09 | ns |
| 90 | 1.43 ± 0.18 | 1.77 ± 0.18 | * |
| 120 | 1.52 ± 0.11 | 2.01 ± 0.11 | ns |
| 150 | 1.54 ± 0.15 | 1.80 ± 0.15 | ns |
| 180 | 1.57 ± 0.17 | 2.25 ± 0.17 | ns |

The results represent the mean of the tumor/reference zone fluorescence ratios obtained at various times for 3 mice.
* corresponds to a significant difference in the ratio between the aptamer and the control sequence measured using a Student's test with P < 0.05.
ns: not significant.

Interestingly, the tumor/reference zone ratio increases more rapidly for the V8 aptamer than for the control sequence and this significant difference is observed as early as 15 minutes after injection (1.51±0.04 for the V8 aptamer and 1.18±0.04 for the control sequence). After 15 minutes, the ratio gradually increases in a similar manner for the aptamer and the control sequence, and the difference between the aptamer and the control sequence then remains constant over time.

2. Three-dimensional Imaging

Three hours after the injection, the amount of aptamers accumulated in the tumors was quantified by tomography. After reconstruction, the fluorescence intensity is visualized in three dimensions in the tumors.

Three hours after injection, the zones corresponding to the tumors were scanned using the Tomofluo3D instrument. After reconstruction using the Imo3D software, the fluorescence intensity was visualized in three dimensions.

It thus appears that the fluorescence intensity is greater in the tumors originating from the mice injected with the V8 aptamer, compared with the mice injected with the control sequence. The accumulation in the tumors 3 hours after injection is therefore greater for the V8 aptamer, suggesting that this accumulation is specific, originating from the binding of the aptamer to its target, the LAR protein.

Figure 10:
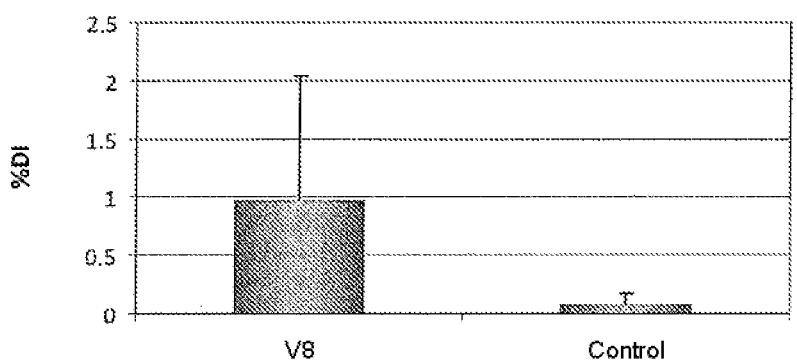
FIG. 10: percentage of the injected dose of V8 aptamer and of a control sequence present in tumors after xenograft of MCF-7 cells The V8 aptamer or a control sequence, which were labeled with Alexa Fluor 680, were injected into mice developing tumors following a subcutaneous injection of MCF-7 cells. Three hours post-injection, the fluorescent signal in the tumor was measured by fluorescent tomography using a TomoFluo 3D instrument.

Using the calibration curves produced by a positron emission tomography (PET)/fluorescence diffuse optical tomography (fDOT) combination, it is possible to quantify a probe labeled with Alexa Fluor 680 present at concentrations between 3 nM and 1 μM (Garofalakis et al. (2010) *Optics Letters* 35: 3024-3026). The percentage of the dose injected (% DI) present in the tumors three hours after injection could therefore be determined in this way (FIG. 10).

Three hours after injection, 0.97±1.1% DI of V8 aptamer is present in the tumor, compared with 0.07±0.11% DI for the control sequence. The accumulation of the aptamer is therefore approximately 10 times greater than that of the control aptamer. It should be noted that the difference observed in three-dimensional imaging is greater than in planar imaging.

Example 4

Use of the V8 Aptamer for Inhibiting Angiogenesis

The inventors tested whether the V8 aptamer could disturb the angiogenesis process by using an in vitro endothelial tube formation test. No role of the LAR protein is known at the current time in angiogenesis; nevertheless, it has been demonstrated that the LAR protein may be involved in the regulation of epithelial cell-cell contacts, and also in the control of the beta-catenin signaling pathways.

Figure 11:
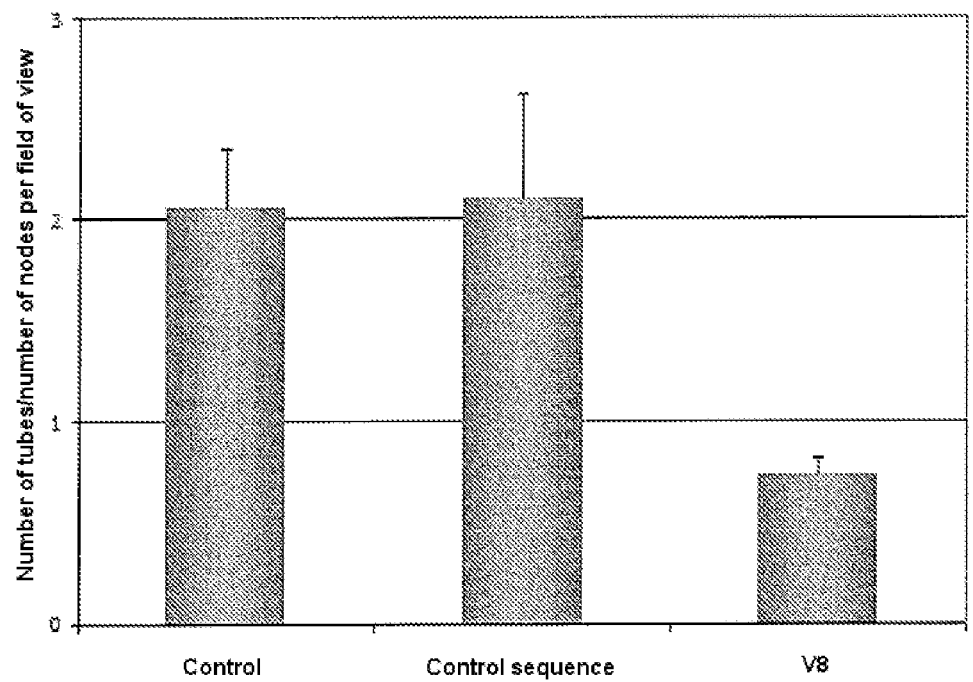
FIG. 11: effect of the V8 aptamer on the formation of endothelial tubes by HUVECs HUVEC cells were cultured in the presence or absence of 5 μM V8 aptamer or of control sequence. After 16 hours of incubation at 37° C. and 5% $CO_2$, the tube formation was evaluated by phase contrast microscopy. The ratio between the number of tubes and the number of nodes visualized per field of view was calculated.

Human umbilical vein endothelial cells (HUVECs) were cultured on Matrigel™ in a medium with a low growth hormone content comprising 2% of fetal calf serum and recombinant basic fibroblast growth factor (bFGF at 3 ng/mL) (Invitrogen). Under these conditions, HUVECs form a network of endothelial tubes which can be observed by microscopy and represents an in vitro model of angiogenesis. The effect of the V8 aptamer on the formation of this network was evaluated (FIG. 11).

It is observed that, after 16 hours of incubation, a network of tubes has formed for the control condition with an average of two tubes formed per node. The V8 aptamer inhibits the formation of tubes with an average of 0.72 tubes per node, whereas the control sequence has no effect, with an average of two tubes per node as for the control condition.

The invention claimed is:

1. An aptamer comprising a nucleic acid comprising, or consisting of:
   a. a sequence of SEQ ID NO: 1, or
   b. a sequence comprising, or consisting of, at least 25 consecutive nucleotides of a sequence having at least 80% identity with SEQ ID NO: 1, wherein the nucleic acid consisting of this sequence binds to the Leukocyte common Antigen-Related Protein Tyrosine Phosphatase (LAR) protein.

2. The aptamer of claim 1, comprising a nucleic acid consisting of the sequence SEQ ID NO: 2.

3. The aptamer of claim 1, wherein the nucleic acid is bonded to at least one additional group.

4. The aptamer of claim 1, wherein the nucleic acid is bonded to at least one additional group and the additional group is selected from the group consisting of a detectable label, a pharmacological compound, and a compound which modifies the pharmacokinetic characteristics of a nucleic acid to which it is bonded.

5. The aptamer of claim 1, wherein the aptamer consists of the nucleic acid and of at least one additional group.

6. A pharmaceutical or diagnostic composition comprising, as active substance, at least one aptamer, in combination with at least one pharmaceutically acceptable vehicle, wherein the aptamer comprises a nucleic acid comprising or consisting of:
   a. the sequence of SEQ ID NO: 1, or
   b. a sequence comprising, or consisting of, at least 25 consecutive nucleotides of a sequence having at least 80% identity with SEQ ID NO: 1, wherein the nucleic acid consisting of this sequence binds to the LAR protein.

7. The pharmaceutical or diagnostic composition of claim 6, wherein the aptamer comprises a nucleic acid consisting of the sequence SEQ ID NO: 2.

8. The pharmaceutical or diagnostic composition of claim 6, wherein the nucleic acid is bonded to at least one additional group.

9. The pharmaceutical or diagnostic composition of claim 6, wherein the nucleic acid is bonded to at least one additional group and the additional group is selected from the group consisting of a detectable label, a pharmacological compound, and a compound which modifies the pharmacokinetic characteristics of a nucleic acid to which it is bonded.

10. An in vitro method for detecting or quantifying LAR protein in a biological sample, comprising:
   a. bringing the biological sample into contact with an aptamer;
   b. quantifying or detecting the presence or absence of aptamer bound in the sample;
   c. deducing therefrom the amount or the presence or absence of LAR protein in the sample,
wherein the aptamer comprises a nucleic acid comprising or consisting of:
   i. the sequence of SEQ ID NO: 1, or
   ii. a sequence comprising, or consisting of, at least 25 consecutive nucleotides of a sequence having at least 80% identity with SEQ ID NO: 1, wherein the nucleic acid consisting of this sequence binds to the LAR protein.

11. The in vitro method of claim 10, wherein the aptamer comprises a nucleic acid consisting of the sequence SEQ ID NO: 2.

12. The in vitro method of claim 10, wherein the nucleic acid is bonded to at least one additional group.

13. The in vitro method of claim 10, wherein the nucleic acid is bonded to at least one additional group and the additional group is selected from the group consisting of a detectable label, a pharmacological compound, and a compound which modifies the pharmacokinetic characteristics of a nucleic acid to which it is bonded.

14. The in vitro method of claim 10, wherein the detection of aptamer bound in the sample is carried out by performing an RT-PCR intended to amplify the aptamer.

15. A method for screening for LAR protein ligands comprising:
   a. bringing together LAR protein and, concomitantly or successively, a ligand to be screened and an aptamer;
   b. determining the amount of aptamer bound to the LAR protein;
   c. deducing therefrom whether the ligand is an LAR protein ligand, wherein the aptamer comprises a nucleic acid comprising or consisting of:
   i. the sequence of SEQ ID NO: 1, or
   ii. a sequence comprising, or consisting of, at least 25 consecutive nucleotides of a sequence having at least 80% identity with SEQ ID NO: 1, wherein the nucleic acid consisting of this sequence binds to the LAR protein.

16. The screening method of claim 15, wherein the aptamer comprises a nucleic acid consisting of the sequence SEQ ID NO: 2.

17. The screening method of claim 15, wherein the nucleic acid is bonded to at least one additional group.

18. The screening method of claim 15, wherein the nucleic acid is bonded to at least one additional group and the additional group is selected from the group consisting of a detectable label, a pharmacological compound, and a compound which modifies the pharmacokinetic characteristics of a nucleic acid to which it is bonded.

19. A method for diagnosis of a cancer in an individual, comprising the following steps:
   a. administering an aptamer according to the invention to the individual;
   b. detecting, quantifying or localizing the aptamer in the individual or a part of the individual;
   c. deducing therefrom whether the individual is suffering from a cancer, wherein the aptamer comprises a nucleic acid comprising or consisting of:
   i. the sequence of SEQ ID NO: 1, or
   ii. a sequence comprising, or consisting of, at least 25 consecutive nucleotides of a sequence having at least 80% identity with SEQ ID NO: 1, wherein the nucleic acid consisting of this sequence binds to the LAR protein.

20. The diagnosis method of claim 19, wherein the aptamer comprises a nucleic acid consisting of the sequence SEQ ID NO: 2.

* * * * *

SEQUENCE LISTING

<160> NUMBER OF SEQ ID NOS: 5

<210> SEQ ID NO 1
<211> LENGTH: 50
<212> TYPE: RNA
<213> ORGANISM: Artificial sequence
<220> FEATURE:
<223> OTHER INFORMATION: Anti-LAR aptamer

<400> SEQUENCE: 1
acugucccag uaugacgcga cugcuuaggu gggauguuuc ccaugccucg          50

<210> SEQ ID NO 2
<211> LENGTH: 97
<212> TYPE: RNA
<213> ORGANISM: Artificial sequence
<220> FEATURE:
<223> OTHER INFORMATION: Anti-LAR aptamer

<400> SEQUENCE: 2
gggagaugcu cugucagacu acgacugucc caguaugacg cgacugcuua ggugggaugu          60
uucccaugcc ucgacuggcu ggcagguuga ugacaag          97

<210> SEQ ID NO 3
<211> LENGTH: 1907
<212> TYPE: PRT
<213> ORGANISM: Homo sapiens

<400> SEQUENCE: 3

```
Met Ala Pro Glu Pro Ala Pro Gly Arg Thr Met Val Pro Leu Val Pro
1               5                   10                  15

Ala Leu Val Met Leu Gly Leu Val Ala Gly Ala His Gly Asp Ser Lys
            20                  25                  30

Pro Val Phe Ile Lys Val Pro Glu Asp Gln Thr Gly Leu Ser Gly Gly
        35                  40                  45

Val Ala Ser Phe Val Cys Gln Ala Thr Gly Glu Pro Lys Pro Arg Ile
    50                  55                  60

Thr Trp Met Lys Lys Gly Lys Lys Val Ser Ser Gln Arg Phe Glu Val
65                  70                  75                  80

Ile Glu Phe Asp Asp Gly Ala Gly Ser Val Leu Arg Ile Gln Pro Leu
                85                  90                  95

Arg Val Gln Arg Asp Glu Ala Ile Tyr Glu Cys Thr Ala Thr Asn Ser
            100                 105                 110

Leu Gly Glu Ile Asn Thr Ser Ala Lys Leu Ser Val Leu Glu Glu Glu
        115                 120                 125

Gln Leu Pro Pro Gly Phe Pro Ser Ile Asp Met Gly Pro Gln Leu Lys
    130                 135                 140

Val Val Glu Lys Ala Arg Thr Ala Thr Met Leu Cys Ala Ala Gly Gly
145                 150                 155                 160

Asn Pro Asp Pro Glu Ile Ser Trp Phe Lys Asp Phe Leu Pro Val Asp
                165                 170                 175

Pro Ala Thr Ser Asn Gly Arg Ile Lys Gln Leu Arg Ser Gly Ala Leu
            180                 185                 190

Gln Ile Glu Ser Ser Glu Glu Ser Asp Gln Gly Lys Tyr Glu Cys Val
        195                 200                 205

Ala Thr Asn Ser Ala Gly Thr Arg Tyr Ser Ala Pro Ala Asn Leu Tyr
    210                 215                 220

Val Arg Val Arg Arg Val Ala Pro Arg Phe Ser Ile Pro Pro Ser Ser
```

```
            225                 230                 235                 240
        Gln Glu Val Met Pro Gly Gly Ser Val Asn Leu Thr Cys Val Ala Val
                        245                 250                 255
        Gly Ala Pro Met Pro Tyr Val Lys Trp Met Met Gly Ala Glu Glu Leu
                        260                 265                 270
        Thr Lys Glu Asp Glu Met Pro Val Gly Arg Asn Val Leu Glu Leu Ser
                        275                 280                 285
        Asn Val Val Arg Ser Ala Asn Tyr Thr Cys Val Ala Ile Ser Ser Leu
                        290                 295                 300
        Gly Met Ile Glu Ala Thr Ala Gln Val Thr Val Lys Ala Leu Pro Lys
        305                 310                 315                 320
        Pro Pro Ile Asp Leu Val Val Thr Glu Thr Thr Ala Thr Ser Val Thr
                        325                 330                 335
        Leu Thr Trp Asp Ser Gly Asn Ser Glu Pro Val Thr Tyr Tyr Gly Ile
                        340                 345                 350
        Gln Tyr Arg Ala Ala Gly Thr Glu Gly Pro Phe Gln Glu Val Asp Gly
                        355                 360                 365
        Val Ala Thr Thr Arg Tyr Ser Ile Gly Gly Leu Ser Pro Phe Ser Glu
        370                 375                 380
        Tyr Ala Phe Arg Val Leu Ala Val Asn Ser Ile Gly Arg Gly Pro Pro
        385                 390                 395                 400
        Ser Glu Ala Val Arg Ala Arg Thr Gly Glu Gln Ala Pro Ser Ser Pro
                        405                 410                 415
        Pro Arg Arg Val Gln Ala Arg Met Leu Ser Ala Ser Thr Met Leu Val
                        420                 425                 430
        Gln Trp Glu Pro Pro Glu Glu Pro Asn Gly Leu Val Arg Gly Tyr Arg
                        435                 440                 445
        Val Tyr Tyr Thr Pro Asp Ser Arg Arg Pro Pro Asn Ala Trp His Lys
                        450                 455                 460
        His Asn Thr Asp Ala Gly Leu Leu Thr Thr Val Gly Ser Leu Leu Pro
        465                 470                 475                 480
        Gly Ile Thr Tyr Ser Leu Arg Val Leu Ala Phe Thr Ala Val Gly Asp
                        485                 490                 495
        Gly Pro Pro Ser Pro Thr Ile Gln Val Lys Thr Gln Gln Gly Val Pro
                        500                 505                 510
        Ala Gln Pro Ala Asp Phe Gln Ala Glu Val Glu Ser Asp Thr Arg Ile
                        515                 520                 525
        Gln Leu Ser Trp Leu Leu Pro Pro Gln Glu Arg Ile Ile Met Tyr Glu
                        530                 535                 540
        Leu Val Tyr Trp Ala Ala Glu Asp Glu Asp Gln Gln His Lys Val Thr
        545                 550                 555                 560
        Phe Asp Pro Thr Ser Ser Tyr Thr Leu Glu Asp Leu Lys Pro Asp Thr
                        565                 570                 575
        Leu Tyr Arg Phe Gln Leu Ala Ala Arg Ser Asp Met Gly Val Gly Val
                        580                 585                 590
        Phe Thr Pro Thr Ile Glu Ala Arg Thr Ala Gln Ser Thr Pro Ser Ala
                        595                 600                 605
        Pro Pro Gln Lys Val Met Cys Val Ser Met Gly Ser Thr Thr Val Arg
                        610                 615                 620
        Val Ser Trp Val Pro Pro Ala Asp Ser Arg Asn Gly Val Ile Thr Gln
        625                 630                 635                 640
        Gln Tyr Ser Val Ala Tyr Glu Ala Val Asp Gly Glu Asp Arg Gly Arg
                        645                 650                 655
```

His Val Val Asp Gly Ile Ser Arg Glu His Ser Ser Trp Asp Leu Val
              660                 665                 670

Gly Leu Glu Lys Trp Thr Glu Tyr Arg Val Trp Val Arg Ala His Thr
              675                 680                 685

Asp Val Gly Pro Gly Pro Glu Ser Ser Pro Val Leu Val Arg Thr Asp
              690                 695                 700

Glu Asp Val Pro Ser Gly Pro Pro Arg Lys Val Glu Val Glu Pro Leu
705                 710                 715                 720

Asn Ser Thr Ala Val His Val Tyr Trp Lys Leu Pro Val Pro Ser Lys
              725                 730                 735

Gln His Gly Gln Ile Arg Gly Tyr Gln Val Thr Tyr Val Arg Leu Glu
              740                 745                 750

Asn Gly Glu Pro Arg Gly Leu Pro Ile Ile Gln Asp Val Met Leu Ala
              755                 760                 765

Glu Ala Gln Trp Arg Pro Glu Glu Ser Glu Asp Tyr Glu Thr Thr Ile
              770                 775                 780

Ser Gly Leu Thr Pro Glu Thr Thr Tyr Ser Val Thr Val Ala Ala Tyr
785                 790                 795                 800

Thr Thr Lys Gly Asp Gly Ala Arg Ser Lys Pro Lys Ile Val Thr Thr
              805                 810                 815

Thr Gly Ala Val Pro Gly Arg Pro Thr Met Met Ile Ser Thr Thr Ala
              820                 825                 830

Met Asn Thr Ala Leu Leu Gln Trp His Pro Pro Lys Glu Leu Pro Gly
              835                 840                 845

Glu Leu Leu Gly Tyr Arg Leu Gln Tyr Cys Arg Ala Asp Glu Ala Arg
              850                 855                 860

Pro Asn Thr Ile Asp Phe Gly Lys Asp Gln His Phe Thr Val Thr
865                 870                 875                 880

Gly Leu His Lys Gly Thr Thr Tyr Ile Phe Arg Leu Ala Ala Lys Asn
              885                 890                 895

Arg Ala Gly Leu Gly Glu Glu Phe Glu Lys Glu Ile Arg Thr Pro Glu
              900                 905                 910

Asp Leu Pro Ser Gly Phe Pro Gln Asn Leu His Val Thr Gly Leu Thr
              915                 920                 925

Thr Ser Thr Thr Glu Leu Ala Trp Asp Pro Pro Val Leu Ala Glu Arg
              930                 935                 940

Asn Gly Arg Ile Ile Ser Tyr Thr Val Val Phe Arg Asp Ile Asn Ser
945                 950                 955                 960

Gln Gln Glu Leu Gln Asn Ile Thr Thr Asp Thr Arg Phe Thr Leu Thr
              965                 970                 975

Gly Leu Lys Pro Asp Thr Thr Tyr Asp Ile Lys Val Arg Ala Trp Thr
              980                 985                 990

Ser Lys Gly Ser Gly Pro Leu Ser Pro Ser Ile Gln Ser Arg Thr Met
              995                1000                1005

Pro Val Glu Gln Val Phe Ala Lys Asn Phe Arg Val Ala Ala Ala
       1010                1015                1020

Met Lys Thr Ser Val Leu Leu Ser Trp Glu Val Pro Asp Ser Tyr
       1025                1030                1035

Lys Ser Ala Val Pro Phe Lys Ile Leu Tyr Asn Gly Gln Ser Val
       1040                1045                1050

Glu Val Asp Gly His Ser Met Arg Lys Leu Ile Ala Asp Leu Gln
       1055                1060                1065

```
Pro Asn Thr Glu Tyr Ser Phe Val Leu Met Asn Arg Gly Ser Ser
1070                1075                1080

Ala Gly Gly Leu Gln His Leu Val Ser Ile Arg Thr Ala Pro Asp
1085                1090                1095

Leu Leu Pro His Lys Pro Leu Pro Ala Ser Ala Tyr Ile Glu Asp
1100                1105                1110

Gly Arg Phe Asp Leu Ser Met Pro His Val Gln Asp Pro Ser Leu
1115                1120                1125

Val Arg Trp Phe Tyr Ile Val Val Pro Ile Asp Arg Val Gly
1130                1135                1140

Gly Ser Met Leu Thr Pro Arg Trp Ser Thr Pro Glu Glu Leu Glu
1145                1150                1155

Leu Asp Glu Leu Leu Glu Ala Ile Glu Gln Gly Gly Glu Glu Gln
1160                1165                1170

Arg Arg Arg Arg Arg Gln Ala Glu Arg Leu Lys Pro Tyr Val Ala
1175                1180                1185

Ala Gln Leu Asp Val Leu Pro Glu Thr Phe Thr Leu Gly Asp Lys
1190                1195                1200

Lys Asn Tyr Arg Gly Phe Tyr Asn Arg Pro Leu Ser Pro Asp Leu
1205                1210                1215

Ser Tyr Gln Cys Phe Val Leu Ala Ser Leu Lys Glu Pro Met Asp
1220                1225                1230

Gln Lys Arg Tyr Ala Ser Ser Pro Tyr Ser Asp Glu Ile Val Val
1235                1240                1245

Gln Val Thr Pro Ala Gln Gln Gln Glu Glu Pro Glu Met Leu Trp
1250                1255                1260

Val Thr Gly Pro Val Leu Ala Val Ile Leu Ile Leu Ile Val
1265                1270                1275

Ile Ala Ile Leu Leu Phe Lys Arg Lys Arg Thr His Ser Pro Ser
1280                1285                1290

Ser Lys Asp Glu Gln Ser Ile Gly Leu Lys Asp Ser Leu Leu Ala
1295                1300                1305

His Ser Ser Asp Pro Val Glu Met Arg Arg Leu Asn Tyr Gln Thr
1310                1315                1320

Pro Gly Met Arg Asp His Pro Pro Ile Pro Ile Thr Asp Leu Ala
1325                1330                1335

Asp Asn Ile Glu Arg Leu Lys Ala Asn Asp Gly Leu Lys Phe Ser
1340                1345                1350

Gln Glu Tyr Glu Ser Ile Asp Pro Gly Gln Gln Phe Thr Trp Glu
1355                1360                1365

Asn Ser Asn Leu Glu Val Asn Lys Pro Lys Asn Arg Tyr Ala Asn
1370                1375                1380

Val Ile Ala Tyr Asp His Ser Arg Val Ile Leu Thr Ser Ile Asp
1385                1390                1395

Gly Val Pro Gly Ser Asp Tyr Ile Asn Ala Asn Tyr Ile Asp Gly
1400                1405                1410

Tyr Arg Lys Gln Asn Ala Tyr Ile Ala Thr Gln Gly Pro Leu Pro
1415                1420                1425

Glu Thr Met Gly Asp Phe Trp Arg Met Val Trp Glu Gln Arg Thr
1430                1435                1440

Ala Thr Val Val Met Met Thr Arg Leu Glu Glu Lys Ser Arg Val
1445                1450                1455

Lys Cys Asp Gln Tyr Trp Pro Ala Arg Gly Thr Glu Thr Cys Gly
```

```
            1460                1465                1470

Leu Ile Gln Val Thr Leu Leu Asp Thr Val Glu Leu Ala Thr Tyr
    1475                1480                1485

Thr Val Arg Thr Phe Ala Leu His Lys Ser Gly Ser Ser Glu Lys
    1490                1495                1500

Arg Glu Leu Arg Gln Phe Gln Phe Met Ala Trp Pro Asp His Gly
    1505                1510                1515

Val Pro Glu Tyr Pro Thr Pro Ile Leu Ala Phe Leu Arg Arg Val
    1520                1525                1530

Lys Ala Cys Asn Pro Leu Asp Ala Gly Pro Met Val Val His Cys
    1535                1540                1545

Ser Ala Gly Val Gly Arg Thr Gly Cys Phe Ile Val Ile Asp Ala
    1550                1555                1560

Met Leu Glu Arg Met Lys His Glu Lys Thr Val Asp Ile Tyr Gly
    1565                1570                1575

His Val Thr Cys Met Arg Ser Gln Arg Asn Tyr Met Val Gln Thr
    1580                1585                1590

Glu Asp Gln Tyr Val Phe Ile His Glu Ala Leu Leu Glu Ala Ala
    1595                1600                1605

Thr Cys Gly His Thr Glu Val Pro Ala Arg Asn Leu Tyr Ala His
    1610                1615                1620

Ile Gln Lys Leu Gly Gln Val Pro Pro Gly Glu Ser Val Thr Ala
    1625                1630                1635

Met Glu Leu Glu Phe Lys Leu Leu Ala Ser Ser Lys Ala His Thr
    1640                1645                1650

Ser Arg Phe Ile Ser Ala Asn Leu Pro Cys Asn Lys Phe Lys Asn
    1655                1660                1665

Arg Leu Val Asn Ile Met Pro Tyr Glu Leu Thr Arg Val Cys Leu
    1670                1675                1680

Gln Pro Ile Arg Gly Val Glu Gly Ser Asp Tyr Ile Asn Ala Ser
    1685                1690                1695

Phe Leu Asp Gly Tyr Arg Gln Gln Lys Ala Tyr Ile Ala Thr Gln
    1700                1705                1710

Gly Pro Leu Ala Glu Ser Thr Glu Asp Phe Trp Arg Met Leu Trp
    1715                1720                1725

Glu His Asn Ser Thr Ile Ile Val Met Leu Thr Lys Leu Arg Glu
    1730                1735                1740

Met Gly Arg Glu Lys Cys His Gln Tyr Trp Pro Ala Glu Arg Ser
    1745                1750                1755

Ala Arg Tyr Gln Tyr Phe Val Val Asp Pro Met Ala Glu Tyr Asn
    1760                1765                1770

Met Pro Gln Tyr Ile Leu Arg Glu Phe Lys Val Thr Asp Ala Arg
    1775                1780                1785

Asp Gly Gln Ser Arg Thr Ile Arg Gln Phe Gln Phe Thr Asp Trp
    1790                1795                1800

Pro Glu Gln Gly Val Pro Lys Thr Gly Glu Gly Phe Ile Asp Phe
    1805                1810                1815

Ile Gly Gln Val His Lys Thr Lys Glu Gln Phe Gly Gln Asp Gly
    1820                1825                1830

Pro Ile Thr Val His Cys Ser Ala Gly Val Gly Arg Thr Gly Val
    1835                1840                1845

Phe Ile Thr Leu Ser Ile Val Leu Glu Arg Met Arg Tyr Glu Gly
    1850                1855                1860
```

| | | | | | | | | | | | |
|---|---|---|---|---|---|---|---|---|---|---|---|
| Val | Val | Asp | Met | Phe | Gln | Thr | Val | Lys | Thr | Leu | Arg | Thr | Gln | Arg |
| | 1865 | | | | | 1870 | | | | | 1875 | | | |
| Pro | Ala | Met | Val | Gln | Thr | Glu | Asp | Gln | Tyr | Gln | Leu | Cys | Tyr | Arg |
| | 1880 | | | | | 1885 | | | | | 1890 | | | |
| Ala | Ala | Leu | Glu | Tyr | Leu | Gly | Ser | Phe | Asp | His | Tyr | Ala | Thr |
| | 1895 | | | | | 1900 | | | | | 1905 | | | |

<210> SEQ ID NO 4
<211> LENGTH: 24
<212> TYPE: DNA
<213> ORGANISM: Artificial sequence
<220> FEATURE:
<223> OTHER INFORMATION: PCR Primer

<400> SEQUENCE: 4
cttgtcatca acctgccagc cagt     24

<210> SEQ ID NO 5
<211> LENGTH: 23
<212> TYPE: DNA
<213> ORGANISM: Artificial sequence
<220> FEATURE:
<223> OTHER INFORMATION: PCR Primer

<400> SEQUENCE: 5
gggagatgct ctgtcagact acg      23